(12) United States Patent
Anderson

(10) Patent No.: US 10,285,717 B2
(45) Date of Patent: May 14, 2019

(54) FECAL MATTER REMOVING TOOL

(71) Applicant: Wayne L. Anderson, Wesley Chapel, FL (US)

(72) Inventor: Wayne L. Anderson, Wesley Chapel, FL (US)

(*) Notice: Subject to any disclaimer, the term of this patent is extended or adjusted under 35 U.S.C. 154(b) by 253 days.

(21) Appl. No.: 14/833,555

(22) Filed: Aug. 24, 2015

(65) Prior Publication Data

US 2016/0058457 A1 Mar. 3, 2016

Related U.S. Application Data

(60) Provisional application No. 62/045,101, filed on Sep. 3, 2014.

(51) Int. Cl.
*A61B 17/22* (2006.01)

(52) U.S. Cl.
CPC .... *A61B 17/22* (2013.01); *A61B 2017/22037* (2013.01)

(58) Field of Classification Search
CPC .......... A61B 2017/22037; A61B 2017/00287; A61B 2017/00685; A61B 2017/2212; A61B 17/22; A61B 17/221; A61B 17/28; A61B 17/320725; A61B 17/320758; A61B 17/44; A61B 90/00; A61M 3/02; A61M 3/0279; A61M 29/00
See application file for complete search history.

(56) References Cited

U.S. PATENT DOCUMENTS

| | | | | |
|---|---|---|---|---|
| 3,583,455 A | * | 6/1971 | Ostrowsky | A47J 43/25 241/100 |
| 3,885,696 A | * | 5/1975 | Eberhardt | B65D 41/0442 215/332 |
| 4,177,811 A | * | 12/1979 | Alvarez | A61M 35/003 15/104.93 |
| 4,243,037 A | | 1/1981 | Smith | |
| 5,000,750 A | | 3/1991 | Leveen et al. | |
| 5,702,404 A | | 12/1997 | Willingham | |
| 5,730,726 A | | 3/1998 | Klingenstein | |
| 6,135,375 A | * | 10/2000 | Kaposi | A47J 45/063 241/273.1 |
| 8,105,335 B1 | * | 1/2012 | Bentley | A61B 17/22 604/106 |
| 2007/0213634 A1 | * | 9/2007 | Teague | A61B 10/0266 600/564 |

* cited by examiner

*Primary Examiner* — Robert A Lynch
*Assistant Examiner* — Mohamed G Gabr
(74) *Attorney, Agent, or Firm* — Global Intellectual Property Agency, LLC; Daniel Boudwin

(57) ABSTRACT

A fecal matter removing tool for safely removing impacted fecal matter from children and adults. The removing tool includes a hollow, cone shaped barrel having a first end and an open second end, wherein the first end is tapered and can be inserted into a user's rectum and rotated in order to remove impacted fecal matter therefrom. A plurality of apertures are disposed along the barrel, wherein a side of each aperture is raised in order to cut and collect the fecal matter within the hollow interior of the barrel. A lip extends perpendicularly outward from the second end of the barrel in order to prevent the barrel from being positioned too far within a user's rectum. A cap is removably secured to the second end of the barrel so the removing tool can be grasped by a user in order to rotate the barrel within the user's rectum.

5 Claims, 2 Drawing Sheets

FECAL MATTER REMOVING TOOL

CROSS REFERENCE TO RELATED APPLICATION

This application claims the benefit of U.S. Provisional Application No. 62/045,101 filed on Sep. 3, 2014. The above identified patent application is herein incorporated by reference in its entirety to provide continuity of disclosure.

BACKGROUND OF THE INVENTION

Field of the Invention

The present invention relates to fecal matter removing tools. More specifically, the present invention provides a fecal matter removing tool comprising a hollow, cone shaped barrel having a first end and an open second end, wherein the first end is tapered and adapted to be inserted within a user's rectum. The barrel comprises a plurality of raised apertures thereon and adapted to receive fecal matter therethrough. The fecal matter removing tool further comprises a lip extending outward from the second end so as to prevent the barrel from being positioned too far into the user's rectum and a cap disposed on the second end so as to allow a user to rotate the barrel and collect fecal matter therein.

Many individuals experience constipation at one time or another. However, some individuals experience chronic constipation, which can lead to solid, immobile fecal matter lodged within a person's rectum, also referred to as fecal impaction. Fecal impaction is uncomfortable and even painful, especially for children. As a result, some individuals resort to various medications and laxatives. Unfortunately, such medications and laxatives can be ineffective and unhealthy if taken on a recurring basis. Therefore, there exists a need in the prior art for a device that can be utilized to manually remove fecal matter from a user in an effective and painless manner.

Devices have been disclosed in the prior art that relate to fecal matter removing tools. These include devices that have been patented and published in patent application publications. These devices generally relate to a shaft having spines or other extracting elements extending from the shaft, such as U.S. Pat. Nos. 5,730,726, 8,105,335, and 5,000,750. Another device, U.S. Pat. No. 4,243,037, generally relates to a syringe having prongs on an end to be inserted into a rectum, wherein the syringe is adapted to dispense enema solution into a user's rectum and the prongs are adapted to pull out fecal matter therefrom. Another device, U.S. Pat. No. 5,702,404, generally relates to an elongated arm having a pair of spoon-like ends adapted to pull out fecal matter from one's rectum.

These prior art devices have several known drawbacks. The devices in the prior art fail to disclose a hollow barrel having raised apertures extending along the barrel, wherein the apertures can cut through the fecal matter and collect the fecal matter within the barrel. Some devices include spines or blades disposed on a shaft in order to break up fecal matter, however, no containment apparatus is provided to collect the pieces of fecal matter therein. Thus the prior art devices fail to disclose a fecal matter removing tool that cuts fecal matter and collects fecal matter within a hollow barrel.

In light of the devices disclosed in the prior art, it is submitted that the present invention substantially diverges in design elements from the prior art and consequently it is clear that there is a need in the art for an improvement to existing fecal matter removing tools. In this regard the instant invention substantially fulfills these needs.

SUMMARY OF THE INVENTION

In view of the foregoing disadvantages inherent in the known types of fecal matter removing tools now present in the prior art, the present invention provides a new fecal matter removing tool wherein the same can be utilized for providing convenience for the user when removing fecal matter within their rectum as a result of constipation or fecal impaction.

It is therefore an object of the present invention to provide a new and improved fecal matter removing tool that has all of the advantages of the prior art and none of the disadvantages.

It is another object of the present invention to provide a fecal matter removing tool comprising a hollow, cone shaped barrel having a first end and an open second end, wherein the first end is adapted to be inserted within a user's rectum.

Another object of the present invention is to provide a fecal matter removing tool further comprises a plurality of apertures disposed along the barrel, wherein the apertures are adapted to receive fecal matter therethrough.

Yet another object of the present invention is to provide a fecal matter removing tool wherein an edge of the each aperture is raised in order to cut through and collect the fecal matter within the hollow barrel.

Yet another object of the present invention is to provide a fecal matter removing tool further comprising a lip extending perpendicularly outward from the second end of the barrel so as to prevent the user from inserting the barrel too far into the rectum.

Yet another object of the present invention is to provide a fecal matter removing tool further comprising a cap removably secured to the second end of the barrel and adapted to be grasped so as to allow the user to rotate the barrel within his or her rectum.

Another object of the present invention is to provide a fecal matter removing tool that may be readily fabricated from materials that permit relative economy and are commensurate with durability.

Other objects, features and advantages of the present invention will become apparent from the following detailed description taken in conjunction with the accompanying drawings.

BRIEF DESCRIPTIONS OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

DETAILED DESCRIPTION OF THE INVENTION

Figure 1:
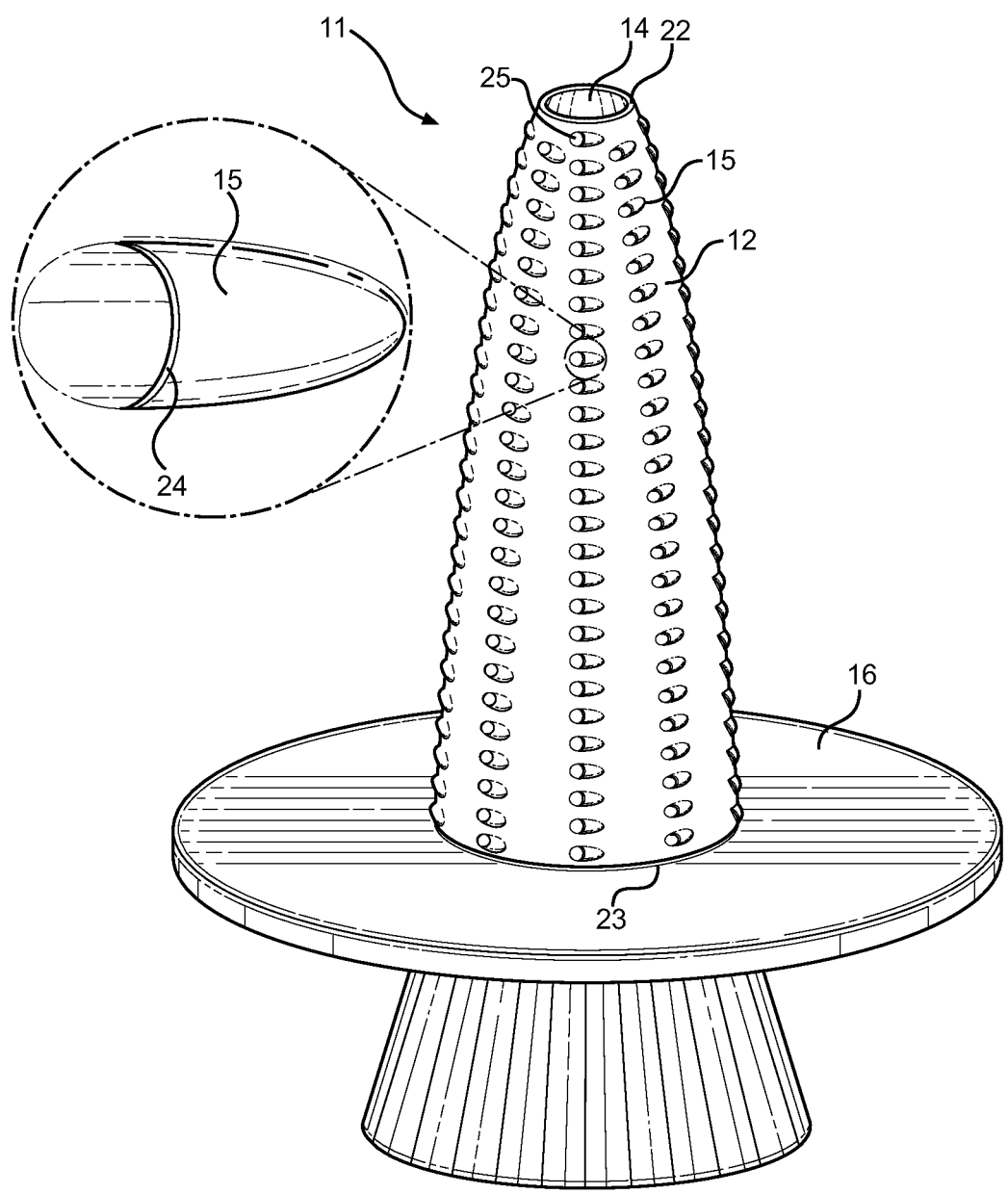
FIG. 1 shows a perspective view of an embodiment of the fecal matter removing tool and a close-up view of an aperture disposed thereon.

Reference is made herein to the attached drawings. Like reference numerals are used throughout the drawings to depict like or similar elements of the fecal matter removing tool. For the purposes of presenting a brief and clear description of the present invention, the preferred embodiment will be discussed as used for manually removing fecal matter from a user's rectum. The figures are intended for representative purposes only and should not be considered to be limiting in any respect.

Referring now to FIG. 1, there is shown a perspective view of an embodiment of the fecal matter removing tool and a close-up view of an aperture disposed thereon. The fecal matter removing tool 11 comprises an elongated, hollow barrel 12 having a first end 22 and a second end 23, wherein the hollow interior is adapted to receive fecal matter therein. The barrel 12 is cone shaped, wherein the first end 22 is tapered and adapted to be inserted into a user's rectum. The second end 23 of the barrel 12 is open so as to allow the fecal matter collected therein to flow towards the open second end to be removed therefrom. Thus, the removing tool 11 may be cleaned for subsequent use. The barrel 12 is preferably composed of a semi-rigid material that prevents injury and avoids puncturing the bowel as it is inserted within the user. In some embodiments, the first end 22 of the barrel 12 comprises an opening 14 in order to receive fecal matter therethrough. Fecal matter can pass through the opening 14 and into the hollow barrel 12 as the barrel is inserted into the user's rectum.

The fecal matter removing tool 11 further comprises a plurality of apertures 15 disposed along the barrel 12 and adapted to receive fecal matter therethrough as the barrel 12 is rotated within the rectum of the user to break apart the impacted fecal matter. Each aperture 15 comprises a raised edge 24 adapted to cut through and collect or scoop pieces of the fecal matter within the hollow barrel 12. In the illustrated embodiment, the raised edges 24 of each aperture 15 are positioned at the same angle as one another. In this way, the fecal matter removing tool 11 is rotated in a single direction, opposite to that of the raised edges 24, so as to allow the raised edges 24 to cut the fecal matter and allow the apertures 15 to receive the fecal matter therethrough.

Preferably, the apertures 15 are disposed in columns 25 along the barrel 12, wherein the apertures 15 are spaced at fixed intervals. The columns 25 are staggered so that the apertures 15 are offset from one another between adjacent columns 25. In this way, more surface area of the fecal matter contacts the raised edges 24 in order to be removed from the rectum.

The second end 23 of the barrel 12 comprises a lip 16 extending perpendicularly outward therefrom. In the illustrated embodiment, the lip 16 is circular in shape, however, in alternate embodiments the lip can comprise any suitable shape so long as the surface of the lip 16 is substantially planar. The planar surface allows the lip 16 to rest on the exterior of a user's anus, thereby providing a barrier so as to prevent the barrel 12 from being inserted too far within the rectum.

Figure 2:
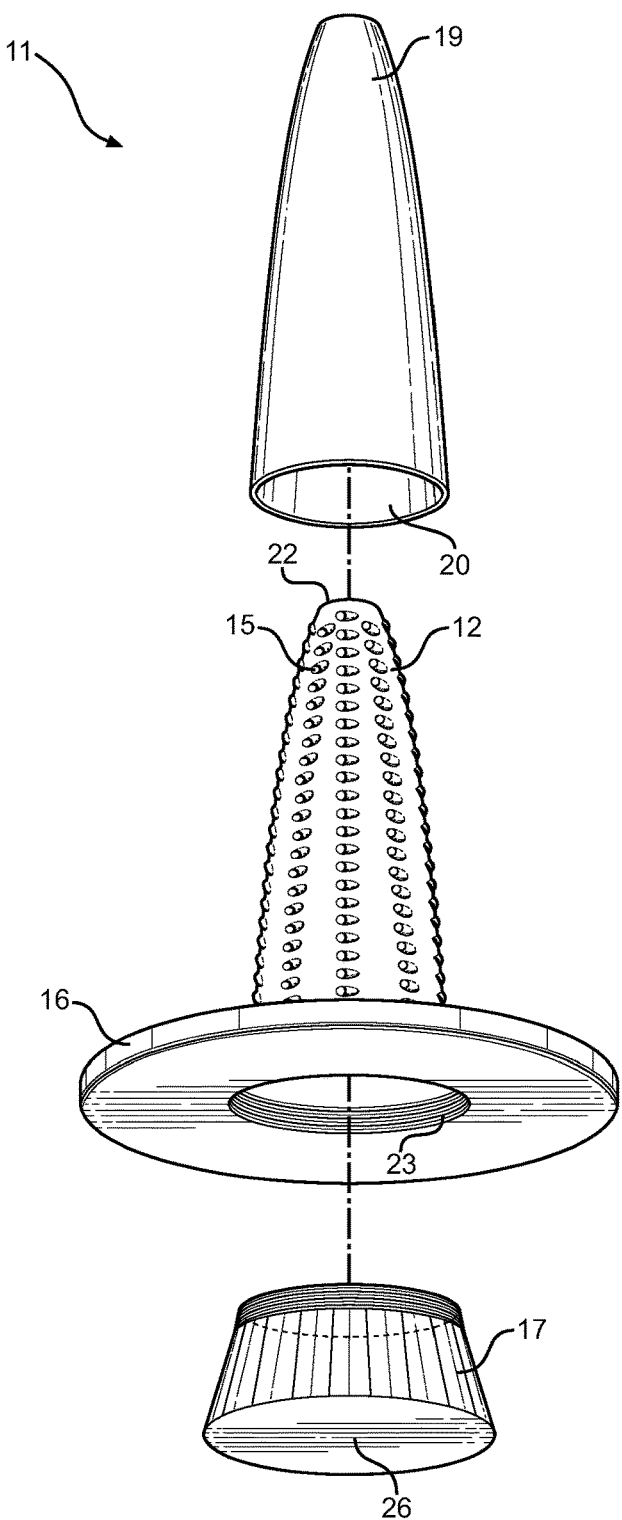
FIG. 2 shows an exploded view an embodiment of the fecal matter removing tool.

Referring now to FIG. 2, there is shown an exploded view an embodiment of the fecal matter removing tool. The fecal matter removing tool 11 further comprises a cap 17 removably secured to the second end 23 of the barrel 12, wherein the cap 17 includes a base 26, one or more sidewalls, and an open upper end, defining an interior volume. The cap 17 is adapted to receive fecal matter that flows into the barrel 12 through the apertures 15 and downward through the second end 23 thereof. Thus, the cap 17 expands the capacity of the removing tool 11 to hold more fecal matter than the size of the barrel 12. Additionally, the separation of the cap 17 from the barrel 12 allows the interior of the barrel 12 to be cleaned. In this way, cleaning liquid can be flushed through the open ends 22, 23 and apertures 15 of the fecal matter removing tool 11.

Preferably, the base 26 of the cap 17 is planar so as to allow the base 26 to rest flush on a horizontal surface so the removing tool can be placed in an upright position when not in use. In the illustrated embodiment, the cap 17 comprises a circular cross section so as to correspond to the circular shaped opening of the second end 23 of the barrel 12. The open upper end of the cap 17 and the open second end 23 of barrel 12 are each threaded so as to removably secure to one another via a screw mechanism. However, in other embodiments, the cap 17 and the second end 23 of the barrel 12 can be removably secured to one another via any suitable fastener, such as female and male mating parts disposed thereon.

The exterior of the cap 17 comprises a plurality of ridges that allow a user to more conveniently grasp the cap 17. In operation, a user grasps the cap 17 and inserts the barrel 12 into his or her rectum. Once the barrel 12 is positioned within the area of fecal impaction, the user twists the cap 17, thereby rotating the barrel 12. As the barrel 12 rotates, the raised edges of the plurality of apertures 15 cut through the fecal matter and collect it within the interior of the barrel 12 and cap 17. After the user has finished using the tool 11, he or she removes the cap 17 and cleans the barrel 12, lip 16, and cap 17.

In some embodiments, the fecal removing tool further comprises a hollow cover 19 having a conical shape with a closed upper end and an open lower end 20, wherein the lower end 20 is adapted to receive the first end of the barrel 12 therein. The cover 19 corresponds to the shape of the barrel 12 and is adapted to removably cover the barrel 12 in order to protect the barrel 12 from germs between uses. However, in other embodiments, the fecal matter removing tool is adapted to be disposed of after each use. Thus, a disposable removing tool comprises a cap 17 that is adapted be grasped and twisted, however, the cap 17 is permanently secured to the second end 23 of the barrel 12.

It is therefore submitted that the instant invention has been shown and described in what is considered to be the most practical and preferred embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A fecal matter removing tool, comprising:
   a hollow semi-rigid barrel having an open first end and an open second end, wherein said open first end is radially tapered such that said barrel extends outwardly from said open first end, such that said open first end is configured for insertion into a user's rectum;

a plurality of apertures disposed in said barrel, wherein said plurality of apertures are arranged in one or more columns, each of the one or more columns are disposed along a longitudinal axis between the open first end and the open second end; wherein each of said plurality of apertures comprises a raised edge configured to cut through said fecal matter in order to collect said fecal matter inside said barrel, wherein said raised edge partially extends over each corresponding aperture, wherein every said raised edge is disposed on a same lateral side and faces perpendicular to said longitudinal axis;

a lip disposed on said open second end of said barrel, wherein said lip extends perpendicularly outwards from said open second end of said barrel;

a cap removably secured to said open second end of said barrel, wherein said cap is configured to be grasped by said user in order to rotate said barrel within said user's rectum, said cap having a planar base and a circular cross section;

a conical shaped cover that corresponds to a shape of said barrel and is adapted to removably cover said barrel.

2. The fecal matter removing tool of claim 1, wherein said plurality of columns are staggered so that said plurality of apertures are offset from one another between adjacent said plurality of columns.

3. The fecal matter removing tool of claim 1, wherein said barrel comprises a conical shape, such that said barrel tapers outwardly along a length from said open first end to said open second end.

4. The fecal matter removing tool of claim 1, wherein said open second end of said barrel and an upper end of said cap are threaded so as to removably secure to one another.

5. The fecal matter removing tool of claim 1, wherein the lip extends entirely around a perimeter defined by the open second end of the barrel.

* * * * *